United States Patent [19]

Hattori et al.

[11] Patent Number: 4,701,305
[45] Date of Patent: Oct. 20, 1987

[54] DEVICE FOR SAMPLING BLOOD AND MEASURING ERYTHROCYTE SEDIMENTATION RATE

[75] Inventors: Hiroyuki Hattori, Kyoto; Takashi Uemura; Toshio Yamauchi, both of Otsu, all of Japan

[73] Assignee: Nissho Corporation, Osaka, Japan

[21] Appl. No.: 878,536

[22] Filed: Jun. 25, 1986

[30] Foreign Application Priority Data

Sep. 6, 1985 [JP] Japan .............................. 60-136786[U]

[51] Int. Cl.⁴ ...................... G01N 33/86; G01N 33/16
[52] U.S. Cl. ........................................ 422/73; 422/99; 422/312; 436/69; 436/70; 436/165; 436/16; 604/317; 604/415; 604/903; 128/764
[58] Field of Search ...................... 436/69, 70, 165, 68, 436/16, 18; 422/73, 312, 99, 101, 102; 128/760, 764; 604/415, 416, 317, 903; 73/863, 864.91

[56] References Cited

U.S. PATENT DOCUMENTS

| | | | |
|---|---|---|---|
| 3,492,096 | 1/1970 | Hattersley | 436/69 |
| 3,734,079 | 5/1973 | Weber | 422/73 |
| 4,071,319 | 1/1978 | Nugent | 422/61 |
| 4,115,068 | 9/1978 | Joslyn | 422/87 |
| 4,392,497 | 7/1983 | Ghaussy . | |

FOREIGN PATENT DOCUMENTS

| | | |
|---|---|---|
| 85/03350 | 8/1985 | PCT Int'l Appl. . |
| 475793 | 9/1969 | Switzerland . |
| 1234044 | 6/1971 | United Kingdom . |
| A2048836 | 12/1980 | United Kingdom . |

Primary Examiner—S. Leon Bashore
Assistant Examiner—Lori-Ann Cody
Attorney, Agent, or Firm—Armstrong, Nikaido, Marmelstein & Kubovcik

[57] ABSTRACT

A device for sampling blood and measuring erythrocyte sedimentation rate. The device comprises a tube with one end closed, a blood sampling portion on an opened end of the tube and an erythrocyte sedimentation rate measuring portion extending from the blood sampling portion. A stopper is located on the open end of said tube, and may be pierced with a blood drawing needle. Finally a partition member is located within said tube and extends substantially over the entire length of said tube. Blood is directly sampled into the device and the device mixes the sampled blood with a solution of an anticoagulant with a high efficiency in the device. Accordingly, measurement of erythrocyte sedimentation rate can be performed quickly and easily.

6 Claims, 9 Drawing Figures

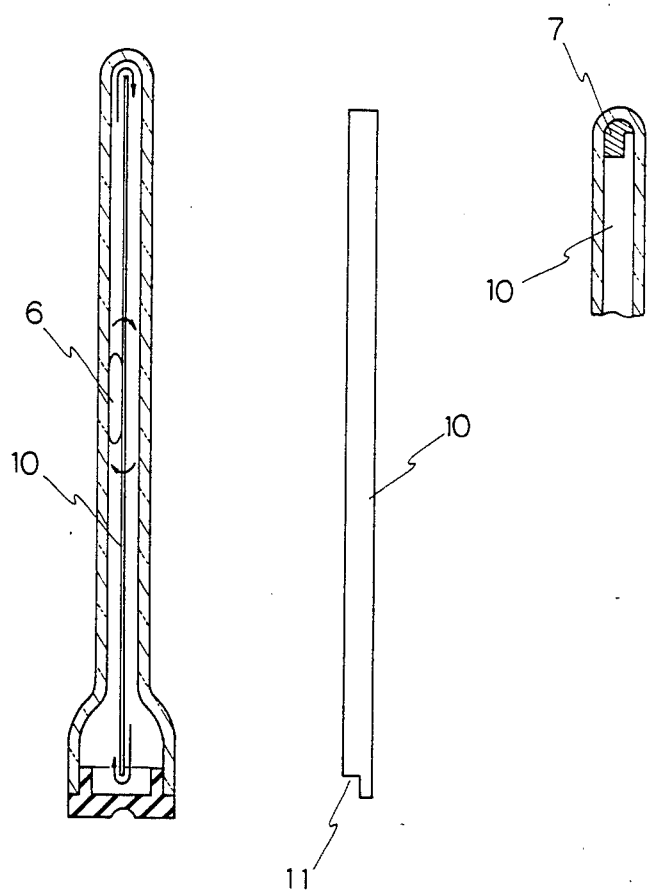

DEVICE FOR SAMPLING BLOOD AND MEASURING ERYTHROCYTE SEDIMENTATION RATE

BACKGROUND OF THE INVENTION

The present invention relates to a device for sampling blood and measuring erythrocyte sedimentation rate. More particularly, it relates to a device which functions as a tube for measuring erythrocyte sedimentation rate as well as functioning as an evacuated tube for sampling blood. That is, the device is designed so that blood can be directly placed into the device from a vein and an erythrocyte sedimentation rate of the sampled blood can be measured in the device without pouring the blood into another measuring tube.

Heretofore, the measurement of erythrocyte sedimentation rate of blood was carried out by sampling blood of the human body by means of a blood sampling device such as an injector, pouring the sampled blood from the blood sampling device into an erythrocyte sedimentation rate measuring device and measuring the erythrocyte sedimentation rate in the measuring device.

However, the conventional method has a drawback that since a measuring device is separate from a blood sampling device, the sampled blood must be poured from the sampling device into the measuring device, which is a troublesome operation.

In order to overcome this drawback, the present applicants disclosed a device serving as a blood sampling tube and as an erythrocyte sedimentation rate measuring tube in Japanese Utility Model Application No. 158997/1984 (filed on Oct. 20, 1984) which was published on May 19, 1986 under Japanese Unexamined Utility Model Publication No. 73303/1986.

The device disclosed in the earlier application is a tube with one end closed; a blood sampling portion on the open end of the tube; an erythrocyte sedimentation rate measuring portion extending from the blood sampling portion. The open end of the tube is stoppered with a stoppering means such as a rubber plug to keep the inside of the tube at a vacuum. The stoppering means can be pierced with a blood drawing needle. A scale for measuring erythrocyte sedimentation rate is provided on the surface of the measuring portion of the tube which is transparent or translucent, or on the surface of a transparent or translucent outer tube in which the measuring tube is inserted. The measurement of an erythrocyte sedimentation rate using the above-mentioned device is carried out as follows: one end of a blood drawing needle is inserted into a vein and other end of the blood drawing needle is inserted into the blood sampling portion of the evacuated tube through the rubber plug. Blood is drawn into the tube through the blood draing needle due to the vacuum in the tube. The blood introduced in the tube is mixed thoroughly with an aqueous solution of an anticoagulant, such as an aqueous solution of sodium citrate, which has been previously placed in the tube. The mixing is effected by turning the tube upside down to allow the blood to flow down to the top of the be in the normal position, followed by repetition of such procedure. After the mixing is completed, the tube is stood vertically on a stand and the measurement is carried out.

With respect to a tube for measuring erythrocyte sedimentation rate, the International Standard relating to the Westergren method provides that the length of a scale portion of the tube be 200 mm.

Accordingly, the measuring portion of the above-mentioned device also must have a length of 200 mm in order to adapt the device for the Westergren method.

On the other hand, it is desirable that the amount of blood used to measure erythrocyte sedimentation rate is as small as possible. In order to reduce the amount of blood used, the inner diameter of the measuring portion of the tube is reduced so long as the length of the measuring portion is 200 mm. For example, when the amount of blood used is less than 3 m, an inner diameter of less than 4.4 mm is required.

However, such smaller diameter of the measuring portion causes an adverse effect on flowing of blood in the abovementioned mixing operation, which requires a long period of time mixing blood with an anticoagulant solution.

It is an object of the present invention to provide a device for sampling blood and measuring erythrocyte sedimentation rate which is capable of sampling blood directly thereinto and mixing the sampled blood with a solution of an anticoagulant quickly and easily.

This and other objects will become apparent from the description hereinafter.

SUMMARY OF THE INVENTION

The present invention provides a device for sampling blood and measuring erythrocyte sedimentation rate which comprises: a tube with one end closed; a blood sampling portion on the opened end of said tube; an erythrocyte sedimentation rate measuring portion extending from said blood sampling portion; a stoppering means for stoppering the open end of said tube to keep the inside of said tube at a vacuum, said stoppering means being capable of being pierced with a blood drawing needle; and a partition member located within and separate from said tube and which extend substantially over the entire length of said tube.

The present inventors have conducted extensive research to solve the above-mentioned problem and found that the slow flow of blood in the above-mentioned mixing operation is attributable to a surface tension on the blood surface and that the adverse influence due to the surface tension can be removed by providing a partition member within the tube.

When the tube is inverted to mix the sampled blood with a solution of an anticoagulant, the partition member destroys the balance of the surface tension on the blood surface, causing the blood to flow quickly.

According to the device of the present invention, blood is directly sampled into the device and the mixing of the sampled blood with a solution of an anticoagulant is performed with a high efficiency in the device. Thus, the operation of measuring erythrocyte sedimentation rate can be performed quickly and easily.

BRIEF DESCRIPTION OF THE DRAWINGS

FIG. 1 is a partially broken side view showing an embodiment of the device of the present invention.

FIG. 2 is a plan view of an embodiment of a partition member used in the present invention.

FIGS. 3 and 4 are explanatory views showing the flow of blood in the device of the present invention.

FIG. 5 is a plan view of another embodiment of the partition member.

FIG. 6 is an explanatory view showing the device wherein the partition member shown in FIG. 5 is installed.

DETAILED DESCRIPTION

The present invention will be explained in detail by referring to the accompanying drawings.

Figures 1, 2, 3:
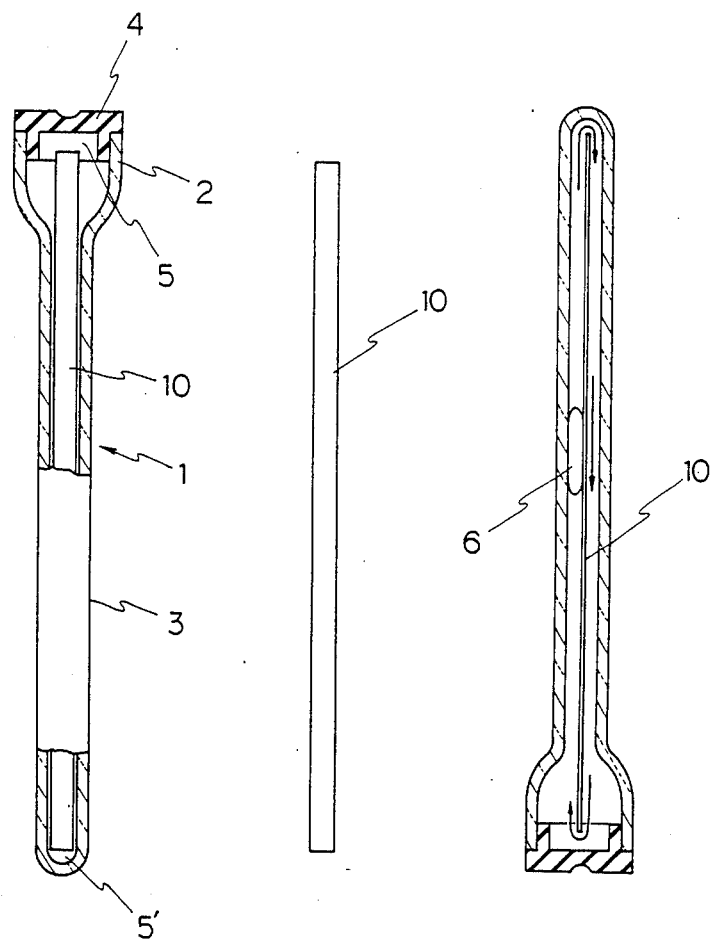

Referring to FIGS. 1 and 2, a device for sampling blood and measuring erythrocyte sedimentation rate in accordance with an embodiment of the present invention comprises a tube 1 with one end closed. The tube 1 comprises a blood sampling portion 2 at the open end of the tube 1 and an erythrocyte sedimentation rate measuring portion 3 extending from the blood sampling portion 2. The measuring portion 3 has the same diameter over the entire length, and the blood sampling portion 2 has a greater diameter than that of the measuring portion 3. A partition member 10 is located within the tube 1. The tube 1 is evacuated in the production step of the device, and the open end of the tube 1 is stoppered with a stoppering means 4 to keep the inside of the tube 1 a vacuum state.

The partition member 10 may have any shape such as plate, pipe or rod. However, a partition member 10 in the form of a plate is preferred, because it produces a loop-like flow of blood in the mixing operation as described below. Hereinafter a plate-shaped partition member 10 is more fully explained.

The partition member 10 preferably has such a length that the top end of the partition member 10 is positioned above the surface of the blood contained in the tube 1 when the tube 1 is stood vertically with the measuring portion 3 on the lower side and there is provided a space 5 between the tope end of the partition member 10 and the stoppering means 4.

The partition member 10 may have such a width that the member 10 can be readily inserted into the measuring portion 3 of the tube 1. However, a partition member 10 having a much smaller width tends to be attached as a whole to the inner wall of the tube 1, so that the member 10 cannot perform its function. From this standpoint, it is preferable that the width of the partition member be substantially equal to or slightly smaller than the inner diameter of the measuring portion 3 of the tube 1.

The thickness of the partition member 10 is preferably not less than 0.2 mm, more preferably from 0.5 to 1 mm.

Any material can be used for the partition member 10, unless it destroys blood cells. However, a transparent or translucent material is preferable, because the measurement is easy. Examples of the material include glass and plastics such as rigid vinyl chloride resin, polypropylene, polystyrene, polyamide, polycarbonate, polymethyl methacrylate and styreneacrylonitrile copolymer.

The tube 1 is made of a transparent or translucent material to make it easy to observe erythrocyte sedimentation rate. Examples of the material include glass and plastics such as polypropylene, acryl resins, polystyrene, butadiene-styrene copolymer (commercially available under the name "ASAFLEX" made by Ashai Chemical Industry Co., Ltd. and "K-Resin" made by Phillips Chemical Company) and styrene-acrylonitrile copolymer.

The inner diameter of the measuring portion 3 preferably ranges from 3 to 6 mm. A measuring portion 3 having an inner diameter of more than 6 mm requires a large amount of blood. A measuring portion 3 having an inner diameter of less than 3 mm makes the mixing of blood difficult. It is preferable that the inner diameter of the blood sampling portion 2 is from 8 to 14 mm, the length of the tube 1 is from 220 to 250 mm, and the volume of blood to be measured is from 1 to 7 ml.

It is preferable that there is provided a space 5' between the lower end of the partition member 10 and the bottom of the tube 1, which readily produces a loop-like flow of blood in the longitudinal direction of the tube 1. This will be explained in detail below.

The effect of the partition member 10 is shown in Test Example 1.

TEST EXAMPLE 1

Ten devices as shown in FIGS. 1 and 2 in accordance with the present invention were provided. The particulars thereof are as follows:

Tube 1
  Entire length: 220 mm
  Inner diameter of the measuring portion 3: 4.25 mm
  Length of the measuring portion 3: 205 mm
Partition member 10
  Shape: plate
  Length: 210 mm
  Width: 4.00 mm
  Thickness: 0.5 mm Into the tube 1 of each device was introduced 2.5 ml of blood. Then the tube 1 was turned upside down. A time required for the air trapped at the one end of the tube 1 to be moved to the other end of the tube 1 was measured.

For comparison, using ten devices wherein no partition member was located in the tube 1, the same procedures as above were repeated.

The results are shown in Table 1.

TABLE 1

| Sample No. | Mixing time | |
|---|---|---|
| | Presence of partition member | Absence of partition member |
| 1 | 3" | 5'32" |
| 2 | 3" | 5'06" |
| 3 | 2" | 4'58" |
| 4 | 3" | 5'45" |
| 5 | 3" | 6'12" |
| 6 | 2" | 5'14" |
| 7 | 2" | 4'20" |
| 8 | 3" | 4'37" |
| 9 | 3" | 6'08" |
| 10 | 3" | 5'13" |
| Average value | 3" | 5'20" |

The results of Table 1 reveal that the use of the partition member exhibits unexpected effect on the speed of mixing of blood.

A test for comparing the device of the present invention with a conventional tube for measuring erythrocyte sedimentation rate was conducted in Test Example 2.

TEST EXAMPLE 2

There were prepared ten devices in accordance with the present invention (the same as those in Test Example 1) and ten Westergren tubes each having an inner diameter of 2.55 mm and a length of 300 mm. Ten blood samples were placed into the tubes and the erythrocyte sedimentation rate thereof were measured. The results are shown in Table 2.

TABLE 2

| Blood Sample No. | Erythrocyte sedimentation distance for an hour (mm) | |
| --- | --- | --- |
|  | The invention | Westergren tube |
| 1 | 5 | 4 |
| 2 | 5 | 5 |
| 3 | 38 | 40 |
| 4 | 67 | 64 |
| 5 | 6 | 6 |
| 6 | 13 | 12 |
| 7 | 91 | 88 |
| 8 | 4 | 5 |
| 9 | 3 | 2 |
| 10 | 25 | 27 |

As is clear from table 2, with respect to the same blood sample, the measurement obtained using the device of the present invention is substantially the same as that obtained using the Westergren tube. Those results reveal that the partition member exerts no adverse effect on the measurement of erythrocyte sedimentation rate.

The partition member 10 used in the present invention will be explained in more detail.

It is preferable that both side ends of the partition member 10 located in the tube 1 come in close contact with the inner wall of the tube 1. When both side ends of the partition member 10 come in close contact with the inner wall of the tube 1, a loop-like flow of blood in the longitudinal direction of the tube 1 is produced as shown in FIG. 3. The numeral 6 indicates an air bubble. However, when both side ends of the partition member 10 do not come in close contact with the inner wall of the tube 1, the blood leaks from the one side of the partition member 10 to the other side of the partition member 10 through a clearance between the side end of the partition member 10 and the inner wall of the tube 1 as shown in FIG. 4, which hinders the formation of the above-mentioned loop-like flow of blood in the longitudinal direction, so that the mixing speed is reduced.

From this standpoint, it is preferable that the width of the partition member 10 is closer to the inner diameter of the tube 1, so long as the partition member 1 is easily inserted into the tube 1. Usually a difference between the inner diameter of the tube 1 and the width of the partition member 10 is selected from 0 to 0.5 mm.

FIG. 5 is a plan view showing another embodiment of the partition member 10 in accordance with the present invention. This partition member 10 has a cut portion 11 at the lower end thereof. A sectional area 7 of blood flow at the lower end of the tube 1 during the mixing operation is enlarged by providing the cut portion 11 as shown in FIG. 6, whereby the flow rate of the blood at that portion is reduced, which results in the prevention of air bubble from being broken into minute air bubbles during the mixing operation. Minute air bubbles tend to remain on the blood surface in the measurement, because they hardly disappear, which causes an error in measurement. However, this defect is overcome by providing the cut portion 11. Further, by providing the cut portion 11, the blood or trapped air starts to move immediately after the tube 1 is turned upside down, which results in incresed mixing speed, though the mechanism thereof is not clear.

It is preferable that a total sectional area including the cut portion 11 between the lower end of the partition member 10 and the inner wall of the lower end of the tube 1, which area is indicated by the numeral 7 in FIG. 6, is about ½ as large as or slightly more than the cross-sectional area of the measuring portion 3 of the tube 1 to exhibit sufficiently the above-mentioned functions.

Figure 7:
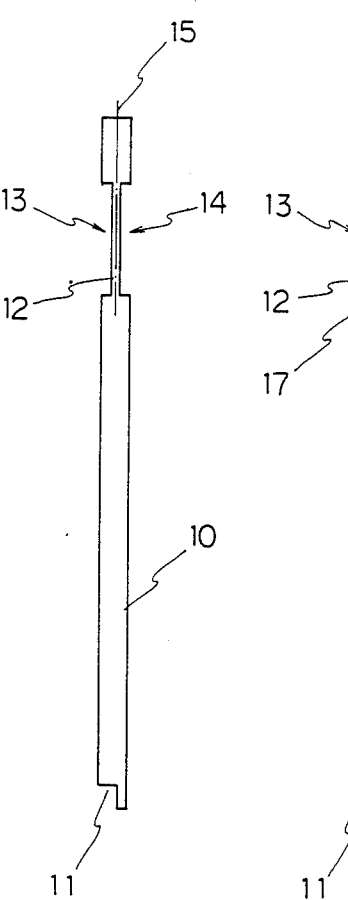
FIG. 7 is a plan view showing a preferred embodiment of the partition member.

FIG. 7 is a plan view showing still another embodiment of the partition member 10 in accordance with the present invention. This partition member 10 has a neck portion 12 at the upper part thereof in addition to the cut portion 11. The neck portion 12 is provided so that the blood surface is positioned at the neck portion 12. The functions of the neck portion 12 are as follows:

(1) In the case of a partition member 10 having no neck portion, a gap between a meniscus level of the blood on the one side of the partition member 10 and a meniscus level of the blood on the other side of the partition member 10 tends to be produced. However, both meniscuses are of the same level by providing the neck portion 12, which ensures an exact measurememt.

(2) When the tube 1 containing a partition member 10 with no neck portion, which is in the inverted position, is turned to the normal position, the blood on the one side of the partition member 10 tends to flow into the other side of the partition member 10 together with air bubbles due to an inertial force. In that case, the air bubbles are divided into minute air bubbles. However, in the case of using the partition member 10 having a neck portion 12, there is produced a blood flow which acts to cancel the flow of blood into the other side of the partition member 10 due to the presence of cut portions 13, 14 on both sides of the neck portion 12, thereby preventing the air bubbles from being divided into minute air bubbles. Thus an exact measurement is ensured.

Usually the width of the neck portion 12 is from ¼ to 1/6 the width of the partition member 10.

The neck portion 12 may be provided such that the cut portion 13 and the cut portion 14 are symmetric with respect to the bisector 15 of the partition member 10 in the longitudinal direction, as shown in FIG. 7.

Figure 8:
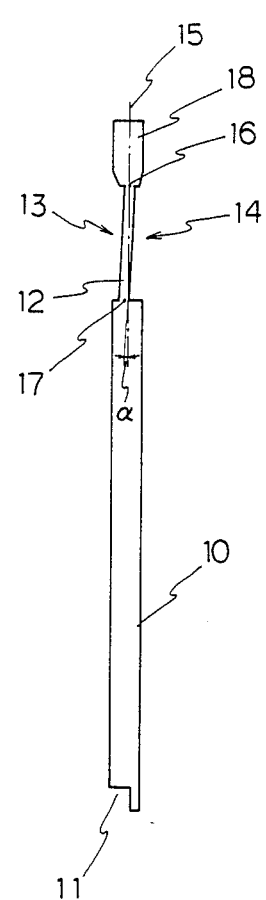
FIG. 8 is a plan view showing the most preferred embodiment of the partition member.

However, as shown in FIG. 8, the neck portion 12 is preferably provided such that the center 16 of the upper end of the neck portion 12 is on the bisector 15 and the center 17 of the lower end of the neck portion 12 is offset rom the bisector 15, whereby the neck portion 12 is inclined against the bisector 15. In that case, the flow rates of the bloods which flow through the cut portion 13 and the cut portion 14 on both sides of the inclined neck portion 12 are different from each other, which causes a disorder of blood flow and reduces the rate of main loop-like blood flow. Thus the above-mentioned flowing of air bubbles into the other side of the partition member 10 is more effectively prevented.

An angle between the neck portion 12 and the bisector 15 is preferably from 1° to 6°.

The neck portion 12 is preferably formed such that a portion 18 which has the same width as that of the major portion of the partition member 10 remains at the upper end portion thereof. The wide end portion 18 functions as follows:

After the mixing operation is completed, some quantity of blood is trapped under the rubber plug 4 and the blood hardly drops due to the surface tension thereof. If the blood is left as it is, there is a danger that the blood drops down gradually along the inner wall of the tube 1, which causes an error in measurement. In contrast thereto, if the wide end portion 18 is positioned beneath the under surface of the rubber plug 4, the blood trapped under the rubber plug 4 drops in a short time along the wide end portion 18.

Figure 9:
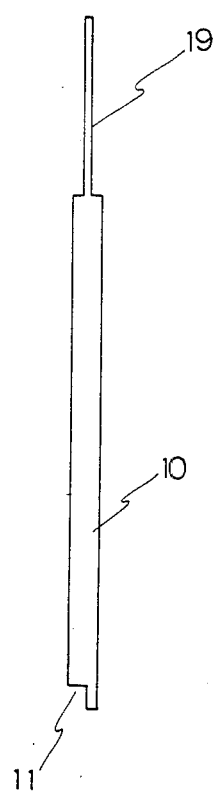
FIG. 9 is a plan view showing still another embodiment of the partition member.

However, the entire upper end portion of the partition member 10 may be narrowed to form a narrow end portion 19, as shown in FIG. 9.

Various partition members were produced and the effects thereof were confirmed as shown in Test Example 3.

TEST EXAMPLE 3

Each partition member 10 was made of a rigid polyvinyl chloride. The entire length was 214 mm and the thickness was 0.5 mm. The other particulars are shown in Table 3. Five species were used with respect to each partition member 10.

The same tube 1 was used.

The following test items were evaluated.

(1) Mixing speed

The mixing speed was measured in the same manner as in Test Example 1.

(2) Start of movement of blood

This was evaluated in terms of the time required for the blood to start to move after the tube 1 was turned upside down.
 ○—Fast
 Δ—Normal
 X—Slow (3) Formation of minute air bubbles It was determined whether or not minute air bubbles were formed during the mixing operation
 ○—No minute air bubbles were formed.
 Δ—A small number of air bubbles were formed.
 X—A large number of minute air bubbles were formed.

(4) Shape of meniscus
 ○—Good
 X—Bad (5) Turning of air bubble

It was determined whether air bubbles on the one side of the partition member 10 flowed into the other side of the partition member 10.
 ○—Turning of air bubble did not occurred.
 X—Turning of air bubble occurred.

(6) Trapping blood

It was determined whether the blood was trapped under the rubber plug 4.
 ○—No blood was trapped.
 Δ—A small quantity of blood was trapped.
 X—A large quantity of blood was trapped.

(7) Total evaluation
 ⊚ —Excellent
 ○ —Good
 Δ—Fair

The results are shown in Table 4.

TABLE 3

|  | A | B | C | D | E | F | G |
|---|---|---|---|---|---|---|---|
| Shape | FIG. 2 | FIG. 2 | FIG. 5 | FIG. 7 | FIG. 7 | FIG. 9 | FIG. 8 |
| Width of partition member (mm) | 3.00 | 4.06 | 4.06 | 4.06 | 4.06 | 4.06 | 4.06 |
| Cut portion 11 (mm × mm) | — | — | 3 × 3 | 3 × 3 | 3 × 3 | 3 × 3 | 3 × 3 |
| Neck portion 12 |  |  |  |  |  |  |  |
| Length (mm) | — | — | — | 10 | 17 | — | 17 |
| Width (mm) | — | — | — | 1 | 1 | — | 1 |
| Inclination angle α (degree) | — | — | — | 0 | 0 | — | 3 |
| Narrow end portion 19 |  |  |  |  |  |  |  |
| Length (mm) | — | — | — | — | — | 26 | — |
| Width (mm) | — | — | — | — | — | 1 | — |
| Inclination angle α (degree) | — | — | — | — | — | 0 | — |

TABLE 4

| Sample | | Partition member | | | | | | |
|---|---|---|---|---|---|---|---|---|
|  | No. | A | B | C | D | E | F | G |
| Mixing speed (sec) | 1 | 6 | 3 | 3 | 3 | 3 | 3 | 3 |
|  | 2 | 4 | 4 | 3 | 2 | 3 | 3 | 2 |
|  | 3 | 7 | 3 | 4 | 4 | 3 | 2 | 3 |
|  | 4 | 5 | 5 | 2 | 2 | 3 | 3 | 3 |
|  | 5 | 2 | 4 | 3 | 2 | 3 | 2 | 3 |
| Start of movement of blood | 1 | X | Δ | ○ | Δ | ○ | ○ | ○ |
|  | 2 | Δ | X | ○ | ○ | Δ | ○ | ○ |
|  | 3 | X | Δ | Δ | Δ | ○ | ○ | ○ |
|  | 4 | Δ | X | ○ | ○ | ○ | Δ | ○ |
|  | 5 |  |  |  |  |  |  | Δ |
| Formation of minute air bubbles | 1 | X | X | X | ○ | ○ | ○ | ○ |
|  | 2 | X | X | X | ○ | Δ | ○ | ○ |
|  | 3 | X | X | ○ | Δ | ○ | Δ | ○ |
|  | 4 | X | X | Δ | Δ | Δ | ○ | ○ |
|  | 5 | X | X | Δ | ○ | ○ | Δ | ○ |
| Shape of meniscus | 1 | X | X | X | ○ | ○ | ○ | ○ |
|  | 2 | X | X | X | ○ | ○ | ○ | ○ |
|  | 3 | X | X | X | ○ | ○ | ○ | ○ |
|  | 4 | X | X | X | ○ | ○ | ○ | ○ |
|  | 5 | X | X | X | ○ | ○ | ○ | ○ |
| Turning of air bubble | 1 | X | X | X | X | ○ | X | ○ |
|  | 2 | X | X | X | ○ | X | X | ○ |
|  | 3 | X | X | X | X | X | ○ | ○ |
|  | 4 | X | X | X | X | X | ○ | ○ |
|  | 5 | X | X | X | ○ | ○ | X | ○ |
| Trapping blood | 1 | ○ | ○ | ○ | ○ | ○ | X | ○ |
|  | 2 | ○ | ○ | ○ | ○ | Δ | X | ○ |
|  | 3 | ○ | ○ | ○ | Δ | ○ | X | ○ |
|  | 4 | ○ | ○ | ○ | ○ | Δ | X | ○ |
|  | 5 | ○ | ○ | ○ | ○ | ○ | X | ○ |
| Total evaluation |  | Δ | Δ | Δ | ○ | ○ | Δ | ⊚ |

As is clear from the results of Table 4, the partition member 10 shown in FIG. 8 which has a width approximately equal to the inner diameter of the measuring portion 3 and has a cut portion 11 at the lower end thereof and an inclined neck portion 12 at the upper end thereof reveals excellent results in all test items.

It is to be understood that the present invention is not limited to the above Examples, and various changes and modifications may be made in the invention without departing from the spirit and scope thereof.

In addition to the elements used in the Examples, other elements can be used in the Examples as set forth in the specification to obtain substantially the same results.

What we claim is:

1. A device for sampling blood and measuring erythrocyte sedimentation rate which comprises:
   a tube with one closed end and one open end;
   said tube having a blood sampling portion provided on the open end of said tube and a scale portion for measuring an erythrocyte sedimentation rate extending from said blood sampling portion;
   a stoppering means for stoppering the open end of said tube to keep the inside of said tube at a vacuum, said stoppering means being capable of being pierced with a blood drawing needle; and
   a plate-shaped partition member located within and separate from said tube and which extends substantially over the entire length of said tube, wherein the width of the partition member is substantially equal to the inner diameter of said scale portion.

2. The device of claim 1, wherein the partition member has a cut portion at the lower end thereof.

3. The device of claim 1, wherein the partition member has a neck portion at the upper end portion thereof, the surface of the blood to be measured being positioned at the neck portion.

4. The device of claim 3, wherein the center of the upper end of the neck portion is substantially on the bisector of the partition member in the longitudinal direction thereof, and the center of the lower end of the neck portion is offset from said bisector, whereby the neck portion is inclined against said bisector.

5. The device of claim 1, wherein the width of the partition member is substantially the same as the inner diameter of said measuring portion, and the partition member has a cut portion at the lower end thereof and a neck portion at the upper end portion thereof, the surface of the blood to be measured being positioned at the neck portion.

6. The device of claim 5, wherein the center of the upper end of the neck portion is substantially on the bisector of the partition member in the longitudinal direction thereof, and the center of the lower end of the neck portion is offset from said bisector, whereby the neck portion is inclined against said bisector.

* * * * *